(12) United States Patent
Hayashi et al.

(10) Patent No.: US 12,678,227 B2
(45) Date of Patent: Jul. 14, 2026

(54) LASER LIGHT IRRADIATION SYSTEM AND LASER LIGHT IRRADIATION METHOD

(71) Applicant: OLYMPUS CORPORATION, Tokyo (JP)

(72) Inventors: Takumi Hayashi, Tokyo (JP); Yuhei Takata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 618 days.

(21) Appl. No.: 17/988,035

(22) Filed: Nov. 16, 2022

(65) Prior Publication Data

US 2023/0083127 A1 Mar. 16, 2023

Related U.S. Application Data

(63) Continuation of application No. PCT/JP2020/019752, filed on May 19, 2020.

(51) Int. Cl.
*A61B 18/26* (2006.01)
*A61B 18/00* (2006.01)

(52) U.S. Cl.
CPC .... *A61B 18/26* (2013.01); *A61B 2018/00732* (2013.01); *A61B 2018/00982* (2013.01); *A61B 2018/263* (2013.01)

(58) Field of Classification Search
CPC .... A61B 2018/00982; A61B 2018/263; A61B 2017/00061; A61B 2017/00176;
(Continued)

(56) References Cited

U.S. PATENT DOCUMENTS 5,632,739 A * 5/1997 Anderson .............. A61B 18/24
606/2
6,022,309 A 2/2000 Celliers et al.
(Continued)

FOREIGN PATENT DOCUMENTS

EP 3308735 A1 4/2018
EP 3610819 A1 2/2020
(Continued)

OTHER PUBLICATIONS

International Search Report dated Jul. 14, 2020 issued in PCT/JP2020/019752.
(Continued)

*Primary Examiner* — John R Downey
*Assistant Examiner* — Karmel J Webster
(74) *Attorney, Agent, or Firm* — Scully, Scott, Murphy & Presser, P.C.

(57) ABSTRACT

A laser light irradiation system that irradiates a stone in a body with laser light to cause the stone to be dust, the laser light irradiation system including a laser fiber that emits the laser light, and a processor configured to control a frequency of the laser light emitted from the laser fiber, wherein the processor is configured to switch between first laser light of a first frequency and second laser light of a second frequency such that the second laser light is emitted at least before or after an emission timing of the first laser light, the first laser
(Continued)

light generating a water flow that pulls the stone toward the laser fiber, the second laser light generating a water flow that stirs the stone.

19 Claims, 13 Drawing Sheets

(58) Field of Classification Search
CPC ........... A61B 2017/00194; A61B 2018/00505; A61B 2018/00642; A61B 2018/00672; A61B 2018/00702; A61B 2018/00708; A61B 2018/00744; A61B 2018/00761; A61B 2018/00904; A61B 18/26; A61B 2018/00732
See application file for complete search history.

(56) References Cited

U.S. PATENT DOCUMENTS

| | | | | |
|---|---|---|---|---|
| 9,895,196 | B2 * | 2/2018 | Waisman | A61B 17/22 |
| 2002/0045890 | A1 | 4/2002 | Celliers et al. | |
| 2015/0289937 | A1 * | 10/2015 | Chia | A61B 1/00009 |
| | | | | 606/2.5 |
| 2015/0313444 | A1 * | 11/2015 | Wolf | A61B 17/22004 |
| | | | | 600/103 |
| 2015/0366571 | A1 * | 12/2015 | Navve | A61B 5/201 |
| | | | | 606/128 |
| 2017/0325890 | A1 | 11/2017 | Chia et al. | |
| 2018/0092693 | A1 * | 4/2018 | Falkenstein | H01S 3/1024 |
| 2018/0303549 | A1 | 10/2018 | Chia et al. | |
| 2020/0000522 | A1 | 1/2020 | Chia et al. | |
| 2021/0137596 | A1 | 5/2021 | Falkenstein et al. | |
| 2022/0079674 | A1 | 3/2022 | Chia et al. | |

FOREIGN PATENT DOCUMENTS

| | | |
|---|---|---|
| JP | H04138150 A | 5/1992 |
| JP | 2000508938 A | 7/2000 |
| JP | 2019531605 A | 10/2019 |
| WO | 1997039690 A1 | 10/1997 |
| WO | 2005094701 A1 | 10/2005 |
| WO | 2013154708 A1 | 10/2013 |
| WO | 2018067530 A1 | 4/2018 |
| WO | 2020033121 A1 | 2/2020 |

OTHER PUBLICATIONS

Blackmon, Richard L. et al., "Fiber-optic manipulation of urinary stone phantoms using holmium: YAG and thulium fiber lasers", Journal of Biomedical Optics (Feb. 2013), vol. 18(2), pp. 028001-1 to 028001-6, SPIE.

Aldoukhi, Ali H. et al., "Endourology and Stones: Understanding the Popcorn Effect During Holmium Laser Lithotripsy for Dusting", Urology (Dec. 2018), vol. 122, pp. 52-57, Elsevier Inc.,https://doi.org/10.1016/j.urology.2018.08.031.

* cited by examiner

PULSE FREQUENCY

LOW
FREQUENCY

HIGH
FREQUENCY

L

H

TIME

DETECT STATE OF STONE

SET CONTROL CONDITION

INPUT CONTROL CONDITION

IRRADIATE STONE WITH LASER LIGHT

END

PULL

RETAIN

STIR

HIT

POWER

TIME

P1

P2

FIRST LASER LIGHT

SECOND LASER LIGHT

LASER LIGHT IRRADIATION SYSTEM AND LASER LIGHT IRRADIATION METHOD

CROSS-REFERENCE TO RELATED APPLICATIONS

This is a continuation of International Application PCT/JP2020/019752, with an international filing date of May 19, 2020, which is hereby incorporated by reference herein in its entirety.

TECHNICAL FIELD

The present invention relates to a laser light irradiation systems and laser light irradiation methods.

BACKGROUND ART

Known technology in the related art involves breaking a kidney stone by using laser light (for example, see Patent Literatures 1 and 2). By being irradiated with the laser light, the stone is fragmented into a desired size by undergoing a large-stone dusting stage (i.e., a dusting stage) and a stage (i.e., a popcorn dusting stage) in which the stone that has been reduced in size by being broken floats randomly.

In the technology described in PTL 1, the first half involves creating a crack in the surface of the stone (dusting) while preventing the stone from floating randomly by reducing the power of the laser light, and the second half involves fragmenting the stone at once (fragmentation) by setting the laser light to high power. PTL 2 describes changing the frequency of the laser light as one of variations for fragmenting the stone by laser irradiation.

CITATION LIST

Patent Literature

PTL 1
U.S. Patent Application Publication No. 2015/0289937
PTL 2
International Publication No. WO 2020/033121

SUMMARY

A first aspect of the present invention provides a laser light irradiation system that irradiates a stone in a body with laser light to cause the stone to be dust, the laser light irradiation system including: a laser fiber that emits the laser light; and a processor configured to control a frequency of the laser light emitted from the laser fiber, wherein the processor is configured to switch between first laser light of a first frequency and second laser light of a second frequency such that the second laser light is emitted at least before or after an emission timing of the first laser light, the first laser light generating a water flow that pulls the stone toward the laser fiber, the second laser light generating a water flow that stirs the stone.

A second aspect of the present invention provides a laser light irradiation method for irradiating a stone in a body with laser light to cause the stone to be dust, the laser light irradiation method including: emitting first laser light of a first frequency that generates a water flow that pulls the stone toward a fiber emission end from which the laser light is emitted; and emitting second laser light of a second frequency that generates a water flow that stirs the stone at least before or after an emission timing of the first laser light.

A third aspect of the present invention provides a method for causing a stone in a body to be dust, the method including: positioning a laser fiber to be directed to the stone, the laser fiber being configured to emit first laser light; keeping the laser fiber at a position while an operation is being performed, the operation making the first laser light emit from the laser fiber to generate a water flow that pulls the stone toward the laser fiber; and performing emission of second laser light that generates a water flow for stirring the stone at least before or after an emission timing of pulling the stone toward the laser fiber.

Advantageous Effects

The present invention is advantageous in that it can allow the energy of the laser to reach the stone without waste.

BRIEF DESCRIPTION OF DRAWINGS

FIG. 4 illustrates how a stone moves when it is irradiated with laser light with a low frequency.

FIG. 15 illustrates a modification of the frequency of the laser light output from the light source.

FIG. 16 illustrates a modification of the pulses of the laser light output from the light source.

DESCRIPTION OF EMBODIMENTS

Since a strong water flow is generated in high-power laser irradiation, if the stone cannot be fragmented at once with high power, the stone floats randomly, resulting in wasteful irradiation of the laser light. When such wasteful laser-light irradiation occurs, the input energy increases accordingly, thus resulting in an increase in the intrarenal temperature of the patient. This is problematic in terms of increased load on the patient. Although some documents may discuss increasing the amount of stone to be dusted and suppressing random floating of the stone, there is no indication about suppressing wasteful irradiation of the laser light.

The present disclosure has been made in view of the circumstances mentioned above, and an object thereof is to provide a laser light irradiation system and a laser light irradiation method that suppress wasteful irradiation of laser light and that achieve a low-invasive laser-based stone dusting treatment.

A laser light irradiation system and a laser light irradiation method according to an embodiment of the present invention will be described below with reference to the drawings.

Figures 1, 2:
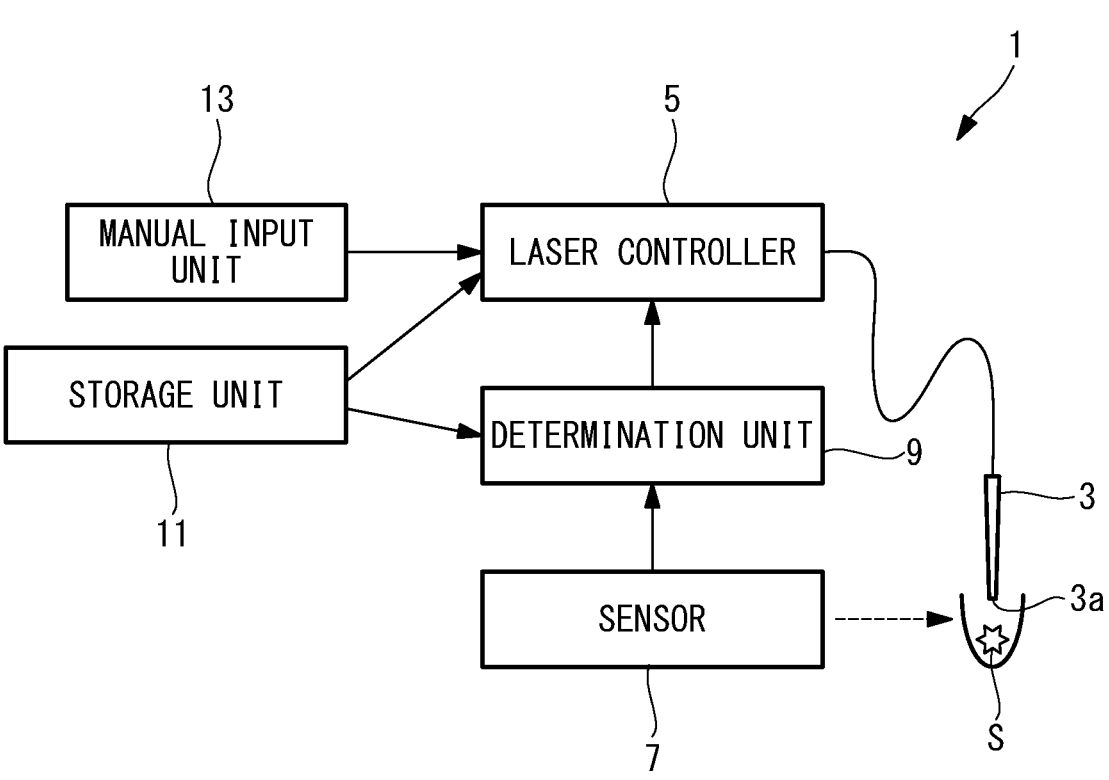
FIG. 1 schematically illustrates the configuration of a laser light irradiation system according to an embodiment of the present invention.
FIG. 2 illustrates the frequency of laser light output from a light source.

As shown in FIG. 1, a laser light irradiation system 1 according to this embodiment irradiates a stone S in a body with laser light so as to cause the stone S to be dust in a liquid.

The laser light irradiation system 1 includes a laser fiber 3 having a fiber emission end 3a that emits laser light, a laser controller (controller) 5 that controls the frequency of the laser light emitted from the fiber emission end 3a, a sensor 7 that detects the state of the stone S, a determination unit 9 that sets a control condition, a storage unit 11 that stores preset data, and a manual input unit 13, such as a mouse or a keyboard. The term "frequency" used here refers to a cyclic frequency of pulses.

The laser fiber 3 may be, for example, a single mode fiber or a multi-mode fiber, or may be a double-clad fiber.

The sensor 7 is, for example, a camera. The sensor 7 acquires, for example, an endoscope image, an X-ray image, or an ultrasound image of the stone S in the liquid. Furthermore, based on the acquired image of the stone S, the sensor 7 acquires information related to the state of the stone S, such as the size, the number, the type, or the shape thereof, as well as information related to the size, the shape, or the gravitational direction of a closed space to be irradiated with the laser light. With regard to the type of the stone S, the composition thereof can be checked by using laser-excited breakdown spectroscopy. The size, the number, and the shape of the stone S can be checked by using, for example, an endoscopic image, an X-ray transmission method, or an ultrasound image.

The determination unit 9 sets an optimal control condition for controlling the frequency of the laser light based on the information acquired by the sensor 7, that is, the information related to the state of the stone S and the state of the space. Because the ease of stirring of the stone S or how the stone S cracks varies depending on the size, the number, the type, and the shape of the stone S, or the size, the shape, and the gravitational direction of the space, the stone S can be made into dust more efficiently with this configuration. The process by the determination unit 9 may be executed by a single processor including hardware.

The storage unit 11 stores therein preset data about a plurality of control conditions for controlling the frequency of the laser light. For example, the preset data may be a collection of optimal laser-light frequencies obtained by preliminarily performing tests while changing the frequency of the laser light for each of the size, the number, the type, and the shape of the stone S, or the size, the shape, and the gravitational direction of the space.

The manual input unit 13 can be used by a user for inputting a desired control condition for controlling the frequency of the laser light. Furthermore, from the control condition set by the user, a control condition stored in the storage unit 11, and a feedback control condition set by the determination unit 9, the user can use the manual input unit 13 to select and set the control condition to be used in control by the laser controller 5.

The laser controller 5 is equipped with a light source that outputs laser light for causing the stone S to be dust. The laser light output from the light source is optically guided by the laser fiber 3 and is subsequently emitted from the fiber emission end 3a.

In accordance with the user's setting, the laser controller 5 receives any one of the control condition input using the manual input unit 13, the control condition stored in the storage unit 11, and the control condition set by the determination unit 9. Then, based on the input control condition, the laser controller 5 switches the laser light to be output from the light source between first laser light or a first pulse train, which generates a water flow that pulls the stone S toward the fiber emission end 3a within a certain range from the fiber emission end 3a, and second laser light or a second pulse train, which generates a water flow that stirs the stone S.

For example, the laser controller 5 causes the first laser light with a first frequency, which is a low frequency, and the second laser light with a second frequency, which is a frequency higher than the first frequency, to be emitted alternately within a range in which the average power of the laser light is between 10 W and 30 W.

Furthermore, as shown in FIG. 2, during an arbitrary cycle C, the laser controller 5 causes the first laser light with a first frequency L to be radiated for a certain time period (first pulse train) and subsequently switches to a second frequency H and causes the second laser light to be radiated for the remaining certain time period (second pulse train). Then, the laser controller 5 repeats this pattern of switching between the first frequency L and the second frequency H. The process by the laser controller 5 may be executed by at least one processor including hardware.

The relationship between the frequency of the laser light and the speed of the water flow, as well as the relationship between the frequency of the laser light and the average power thereof, will now be described.

Figure 3A:
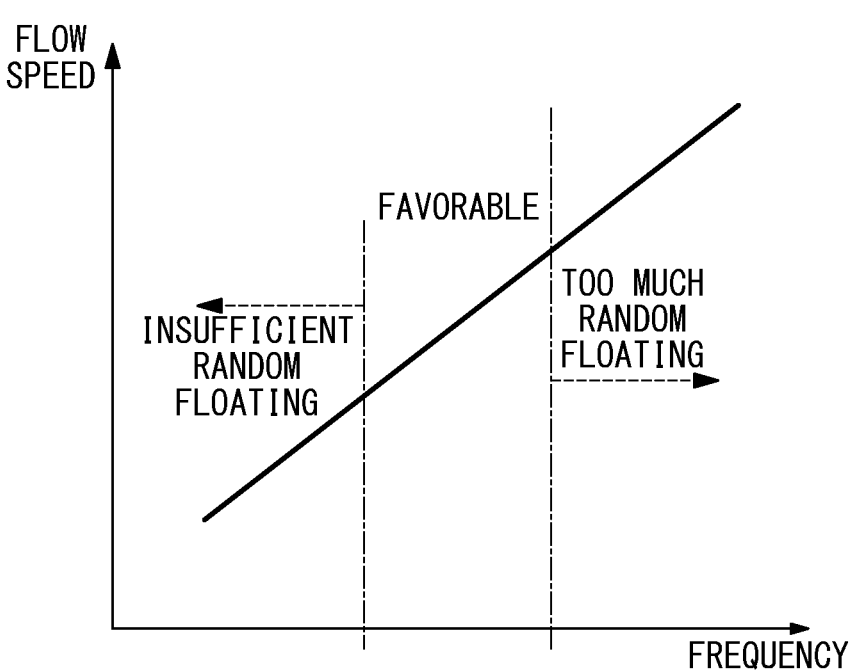
FIG. 3A illustrates the relationship between the frequency of laser light and the speed of a water flow.

For example, as shown in FIG. 3A, if the frequency of the laser light is lower than a certain range, the speed of the water flow generated as a result of the laser-light irradiation is low, so that the stirring of the stone S is too weak. On the other hand, if the frequency of the laser light is higher than the certain range, the speed of the water flow generated as a result of the laser-light irradiation is high, so that the stirring of the stone S is too intense. Therefore, with regard to the stirring of the stone S, it is desirable that the frequency of the laser light be controlled within the certain range, and that a water flow that allows the stone S to float moderately therein be generated.

Figure 3B:
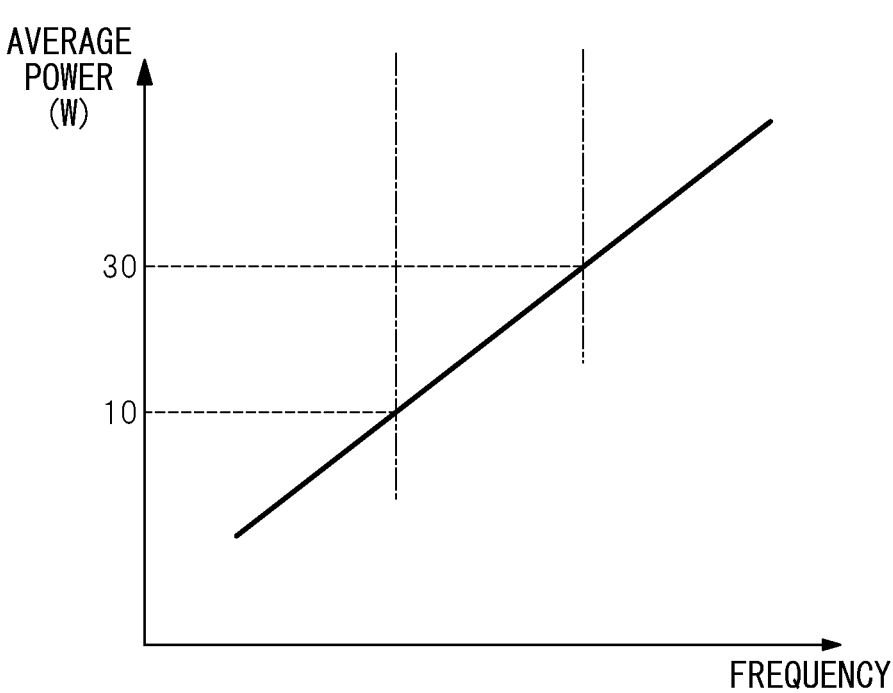
FIG. 3B illustrates the relationship between the average power of laser light and the frequency thereof.

Next, as shown in FIG. 3B, similar to the relationship between the frequency of the laser light and the speed of the water flow shown in FIG. 3A, the relationship between the frequency of the laser light and the average power thereof shows a tendency of increase. In other words, the appropriate range for stirring the stone S can also be expressed with the average power.

The average power when laser light with two different frequencies is repeatedly radiated is expressed with expression (1) indicated below.

{Expression 1}

$$P_{ave} = \frac{P_1 W_1 N_1 + P_2 W_2 N_2}{N_1 f_2 + N_2 f_1} * f_1 f_2 \qquad (1)$$

where $P_{ave}$ denotes the average power, P denotes the peak power, W denotes the pulse width, f denotes the frequency, and N denotes the pulse number.

In the embodiment, the dusting efficiency is improved in all conditions, as compared with the method in the related art with the average power ranging between 10 W and 30 W, and therefore the range between 10 W to 30 W is preferable for achieving appropriate stirring.

Next, the frequency of the laser light and the suction effect will be described.

Figure 4:
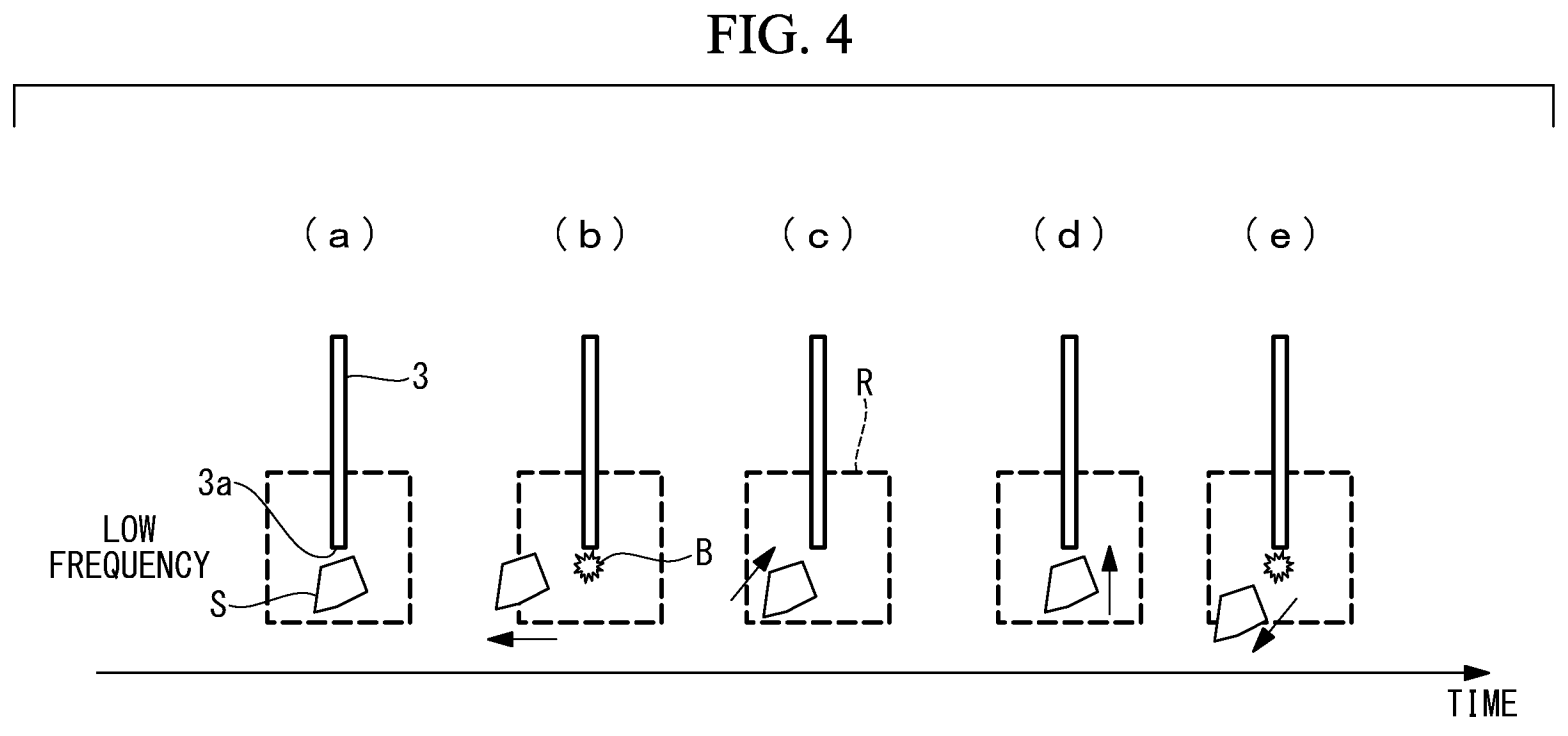

For example, as shown in FIG. 4, when the laser light with the first frequency, which is a low frequency, is first emitted from the fiber emission end 3a in a liquid, a bubble B is generated from the fiber emission end 3a, and the laser light is transmitted through the bubble B, so that the stone S is irradiated with the laser light (i.e., the state in FIG. 4(a)). Then, a dusting impact causes the stone S to move away from the fiber emission end 3a (i.e., the state in FIG. 4(b)).

Subsequently, when the bubble B starts to contract by being cooled by the surrounding liquid, a suction force is generated. As a result, within a certain range R from the fiber emission end 3a, a suction effect occurs in which the stone S within a certain range R is pulled toward the fiber emission end 3a (i.e., the state in FIG. 4(c)).

Subsequently, in the state where the stone S pulled toward the fiber emission end 3a is disposed in the laser-light irradiation range, next laser light is emitted. Accordingly, a bubble B is generated again, and the stone S is irradiated with the laser light transmitted through the bubble B (i.e., the state in FIG. 4(d)). Then, a dusting impact causes the stone S to move away from the fiber emission end 3a again (i.e., the state in FIG. 4(e)).

The first laser light with the low frequency can cause the stone S pulled by the suction effect to be set directly below the fiber emission end 3a. Consequently, the stone S can be irradiated with a larger amount of laser light in subsequent irradiation, thereby reducing wasteful irradiation of laser light.

Figure 5:
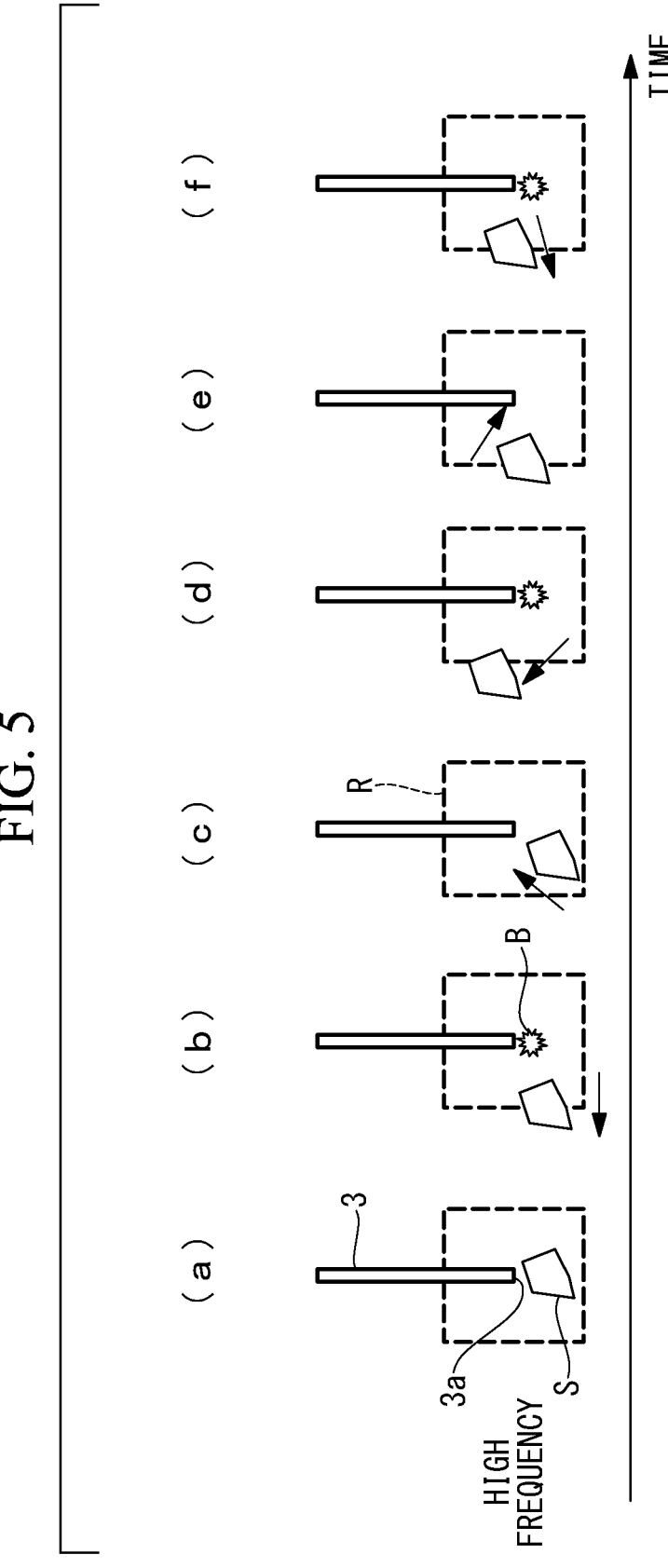
FIG. 5 illustrates how the stone moves when it is irradiated with laser light with a high frequency.

On the other hand, an irradiation interval of the laser light of the second frequency, which is a high frequency, is shorter than the first frequency at which the frequency is low. For example, as shown in FIG. 5, when the laser light with the second frequency is first emitted from the fiber emission end 3a within a liquid, a bubble B is generated from the fiber emission end 3a, and the laser light is transmitted through the bubble B, so that the stone S is irradiated with the laser light (i.e., the state in FIG. 5(a)). Then, a dusting impact causes the stone S to move away from the fiber emission end 3a (i.e., the state in FIG. 5(b)).

Subsequently, when the bubble B starts to contract by being cooled by the surrounding liquid, a suction effect occurs within a certain range R from the fiber emission end 3a. Consequently, the stone S within the certain range R is pulled toward the fiber emission end 3a (i.e., the state in FIG. 5(c)).

However, before the stone S pulled toward the fiber emission end 3a is disposed within the laser-light irradiation range, next laser light is emitted. Therefore, the pulled stone S is not irradiated with the laser light, or the stone S is rotated as a result of an end of the stone S being irradiated with the laser light, thus causing the stone S to move away from the fiber emission end 3a again due to a dusting impact (i.e., the state in FIG. 5(d)).

When the generated bubble B starts to contract, a suction effect occurs so that the stone S is pulled toward the fiber emission end 3a again (i.e., the state in FIG. 5(e)). In this case, next laser light is similarly emitted before the stone S pulled toward the fiber emission end 3a is disposed within the laser-light irradiation range. Therefore, the stone S is not irradiated with the laser light, or the stone S is rotated as a result of an end of the stone S being irradiated with the laser light, thus causing the stone S to move away from the fiber emission end 3a due to a dusting impact (i.e., the state in FIG. 5(f)). Thus, the second frequency, which is a high frequency, tends to lead to wasteful irradiation of laser light.

Next, the frequency of the laser light and the stirring effect of the stone S will be described.

Figure 6:
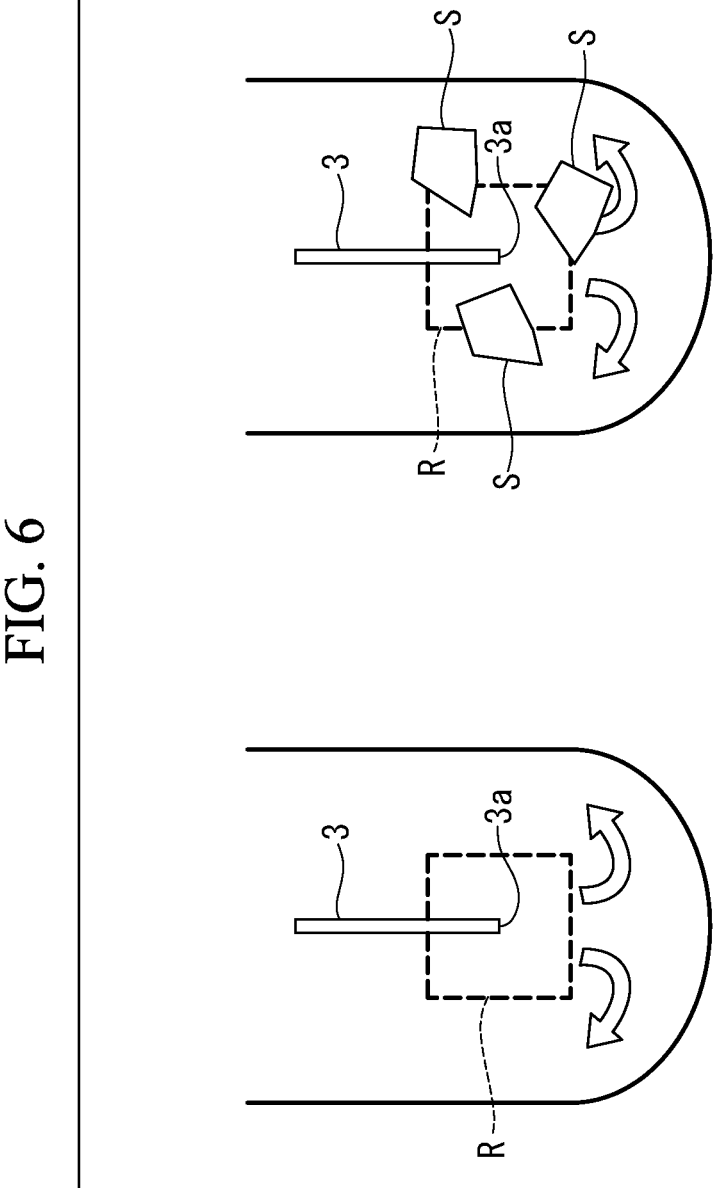
FIG. 6 illustrates a state where the stone is stirred when it is irradiated with laser light with the high frequency.

With the second frequency, which is a high frequency, the irradiation is performed highly frequently. Therefore, as shown in FIG. 6, when the laser light with the second frequency is emitted in a liquid, a strong water flow is generated in front of the fiber emission end 3a (see the left part of FIG. 6). Accordingly, the stone S located in front of the fiber emission end 3a is stirred heavily, so that the stone S is readily disposed within the certain range R that receives the suction effect (see the right part of FIG. 6).

Figure 7:
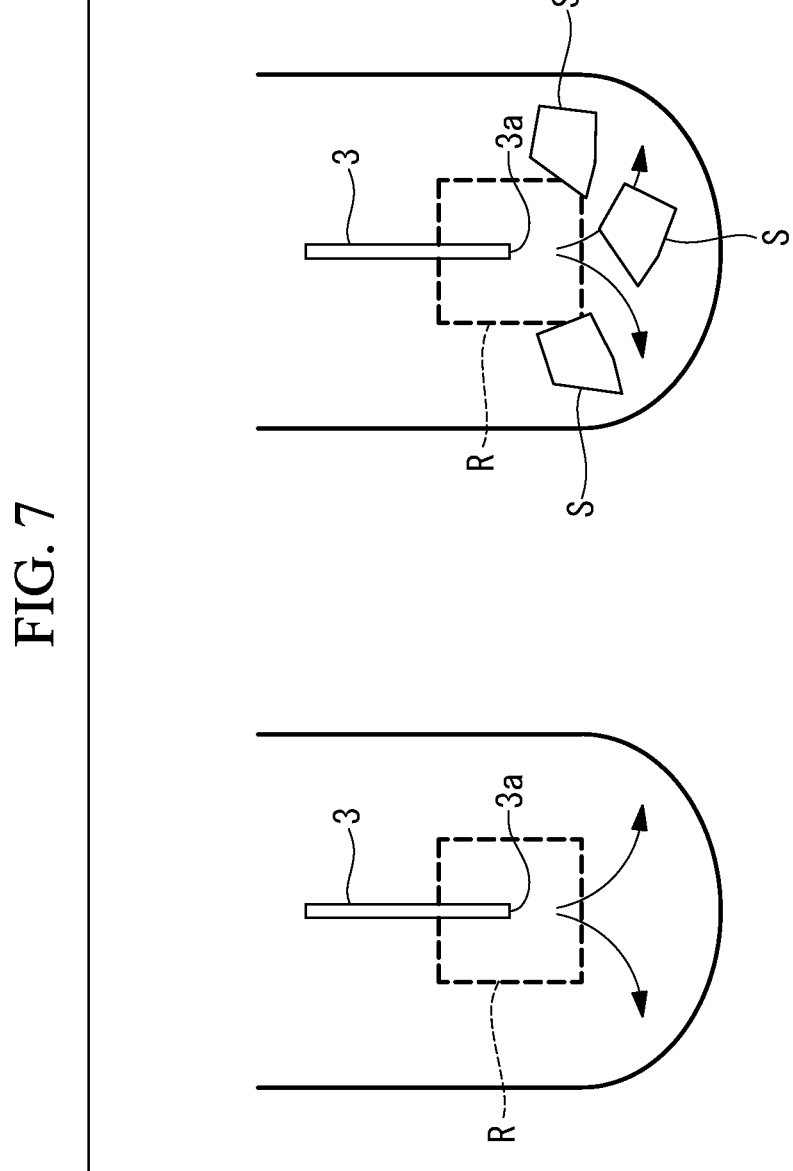
FIG. 7 illustrates a state where the stone is stirred when it is irradiated with laser light with the low frequency.

On the other hand, with the first frequency, which is a low frequency, the irradiation is performed less frequently. Therefore, as shown in FIG. 7, when the laser light with the first frequency is emitted, a weak water flow is generated in front of the fiber emission end 3a (see the left part of FIG. 7). Since the stone S located in front of the fiber emission end 3a is not heavily stirred in a weak water flow, it is difficult for the stone S to enter the certain range R that receives the suction effect (see the right part of FIG. 7).

Next, the laser light irradiation method according to this embodiment will be described.

Figure 8:
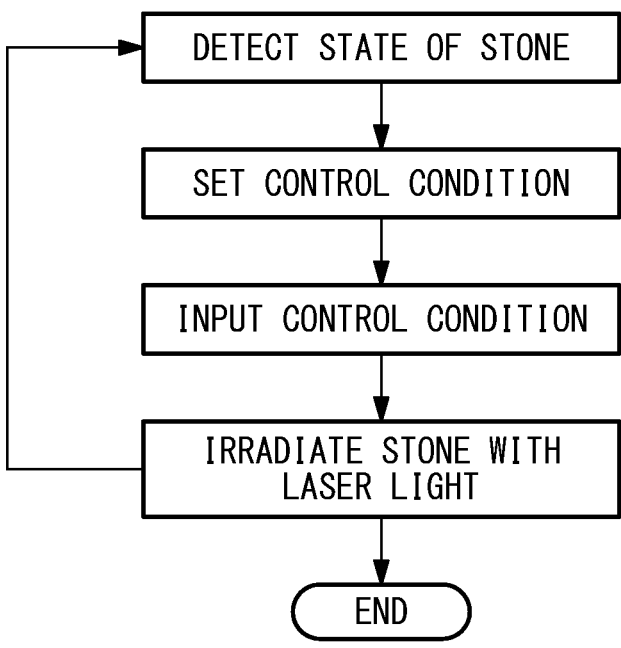
FIG. 8 is a flowchart illustrating a laser light irradiation method according to an embodiment of the present invention.

As shown in a flowchart in FIG. 8, the laser light irradiation method according to this embodiment includes step S1 for causing the sensor 7 to detect the state of the stone S in a case where the control condition set by the determination unit 9 is to be employed, step S2 for causing the determination unit 9 to set the control condition, step S3 for inputting the set control condition to the laser controller 5, and step S4 for emitting laser light based on control by the laser controller 5.

Step S4 involves, by the laser controller 5, performing control to emit first laser light for generating a water flow that pulls the stone S toward the fiber emission end 3a and subsequently emitting second laser light for generating a water flow that stirs the stone S. Steps S1 to S4 are repeated in accordance with the state of the stone S.

Next, the operation of the laser light irradiation system 1 having the above-described configuration and the laser light irradiation method will be described.

In order to cause the stone S to be dust in the body by using the laser light irradiation system 1 and the laser light irradiation method according to this embodiment, the fiber emission end 3a of the laser fiber 3 is first disposed to face the stone S to be treated.

Then, for example, the sensor 7 acquires an image of the stone S to be treated and subsequently acquires information related to the state of the stone S or the state of the space (step S1). The information acquired by the sensor 7 is transmitted to the determination unit 9. Then, based on the information from the sensor 7, the determination unit 9 sets an optimal control condition for controlling the frequency of laser light (step S2).

The interval between the pulses of the first frequency appropriate for pulling the stone S toward the laser-light irradiation range is determined in accordance with, for example, the size of the stone S. Since the frequency for sufficiently pulling a 2-mm stone S to a laser-light irradiation position is approximately 60 Hz, if the stone S is to be dusted to the size of 1 mm, which is one of indicators indicating that the treatment is completed, a frequency of 120 Hz is required. In other words, it is preferable that the first frequency to be selected be 120 Hz or lower. Furthermore, since it is assumable that the stone S may have a size of 2 mm or larger, the use of 0 Hz to 60 Hz is also conceivable. Therefore, the first frequency preferably ranges between 0 Hz and 120 Hz.

The appropriate average power of the laser light required for stirring is determined in accordance with the state of the stone S or the state of the space. Since a change in the size or the shape of the stone S leads to a change in the resistance between stones S, the resistance at the walls of the space, or the resistance against the water flow, the appropriate average power also changes. Since a change in the number of stones S leads to a change in the overall weight of the stone S, the appropriate average power also changes. Since a change in the area of the space leads to a change in the height to which the stone S floats randomly, the appropriate average power also changes. Since a change in the gravitational direction in the space leads to a change in how the stone S stops near the fiber emission end 3a after the stone S is stirred, the appropriate average power also changes.

By using the appropriate first frequency and the appropriate average power determined in step S1, a second frequency (f2) is calculated from expression (1), whereby an optimal laser condition is determined.

Subsequently, the user selects and sets a control condition to be used in the control by the laser controller 5 from a control condition set by the user, a control condition stored in the storage unit 11, and a control condition set by the determination unit 9.

If the control condition set by the determination unit 9 is selected, the control condition is transmitted from the determination unit 9 to the laser controller 5 (step S3). Then, the laser controller 5 causes the light source to emit laser light via the laser fiber 3 based on the input control condition (step S4).

As shown in FIG. 2, step S4 involves irradiating the first laser light with the first frequency L for a certain time period (first pulse train) and then switching the frequency to radiate the second laser light with the second frequency H for the remaining certain time period (second pulse train) during an arbitrary cycle C. Then, this switching pattern is repeated a predetermined number of times.

Figure 9:
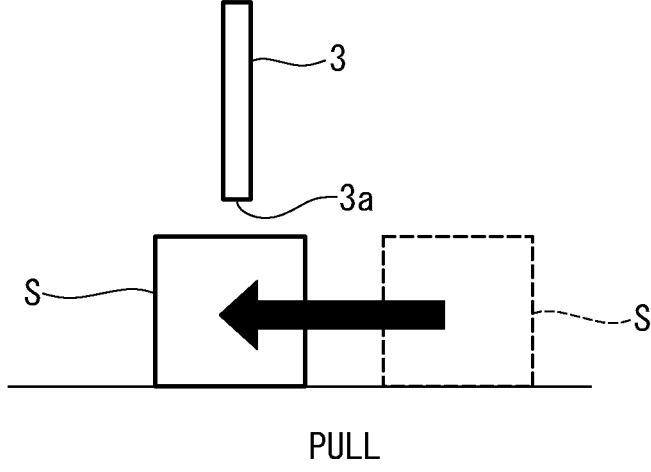
FIG. 9 illustrates a state where the stone is being pulled toward a fiber emission end by being irradiated with laser light.

The first frequency serving as the frequency of the first laser light may be lower than the second frequency serving as the frequency of the second laser light. In this case, when the first laser light with the first frequency, which is a low frequency, is emitted, a bubble is generated from the fiber emission end 3a, and the first laser light emitted in a state where the bubble is in contact with both the fiber emission end 3a and the stone S is transmitted through the bubble and is radiated onto the stone S. Laser light emitted in a state where the bubble is separated from the stone S does not reach the stone. When the bubble starts to disappear, a suction effect occurs so that, for example, the stone S in the certain range R from the fiber emission end 3a is pulled toward the fiber emission end 3a, as shown in FIG. 9, whereby the laser light can readily reach the stone S.

If the interval between the pulses is too short, next laser light is emitted before the stone S pulled toward the fiber emission end 3a is disposed in the laser-light irradiation range. In contrast, with the first frequency, which is a low frequency with a long interval, the next first laser light is emitted in a state where the pulled stone S is disposed in the irradiation range of the first laser light. Accordingly, a bubble is generated from the fiber emission end 3a, and the stone S is irradiated with the first laser light transmitted through the bubble.

Subsequently, the first frequency is switched to the second frequency, so that the second laser light with the high frequency is emitted. In this case, similar to the case of the first frequency, a bubble is generated from the fiber emission end 3a, and the stone S is irradiated with the second laser light transmitted through the bubble.

Figure 10:
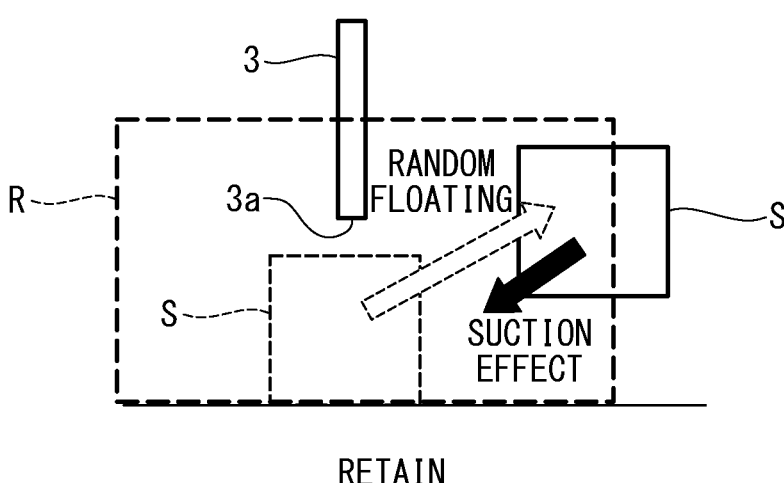
FIG. 10 illustrates a state where the stone is being stopped by being irradiated with laser light.

As shown in FIG. 10, with the second frequency, a dusting impact causes the stone S to float randomly, so that the stone S moves away from the fiber emission end 3a. However, when the bubble disappears and a suction effect occurs, the stone S that has moved away is pulled toward the fiber emission end 3a.

If the interval between the pulses is too long, the stone S that has moved away from the fiber emission end 3a moves out of the certain range R that receives the suction effect. In contrast, with the second frequency, which is a high frequency with a short interval, the stone S can be readily retained within the certain range R that receives the suction effect.

Figure 11:
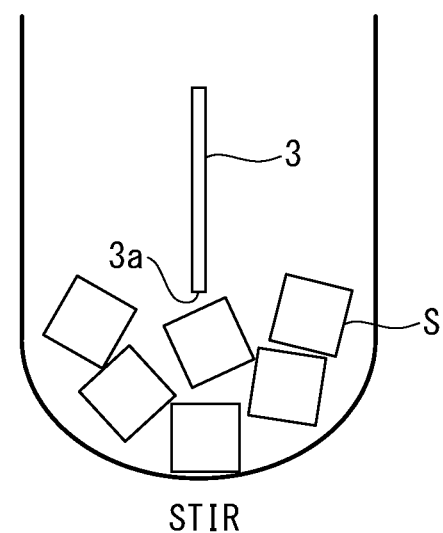
FIG. 11 illustrates a state where the stone is being stirred by being irradiated with laser light.
Figure 12:
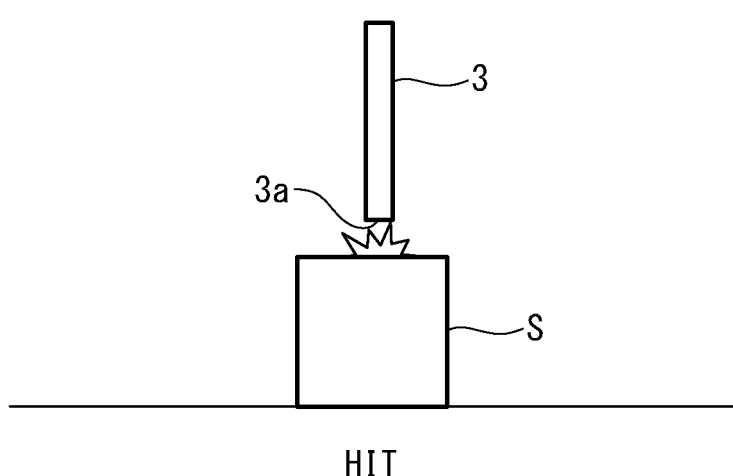
FIG. 12 illustrates a state where the stone is being irradiated with laser light.

Subsequently, when the second laser light is continuously radiated, a large water flow is generated, so that the stone S is stirred, as shown in FIG. 11. Accordingly, the stone S can readily enter the certain range R that receives the suction effect. Then, the second laser light is continuously emitted to the stone S disposed within the certain range R that receives the suction effect. Consequently, as shown in FIG. 12, the stone S is continuously irradiated (hit) with the second laser light.

In a manner which is the same as or similar to that described above, the laser light is radiated onto the stone S while being switched between the first frequency and the second frequency until the stone S is dusted to a desired size, such as a size smaller than 1 mm.

As described above, in the laser light irradiation system 1 and the laser light irradiation method according to this embodiment, the laser controller 5 controls the combination of the emission timing of the first laser light and the emission timing of the second laser light so that the stone S can be readily irradiated with the laser light. Accordingly, wasteful irradiation of laser light that may occur as a result of the laser light being emitted in a state where the stone S is disposed away from the fiber emission end 3a can be suppressed, thereby achieving a low-invasive laser-based stone dusting treatment.

Figure 13:
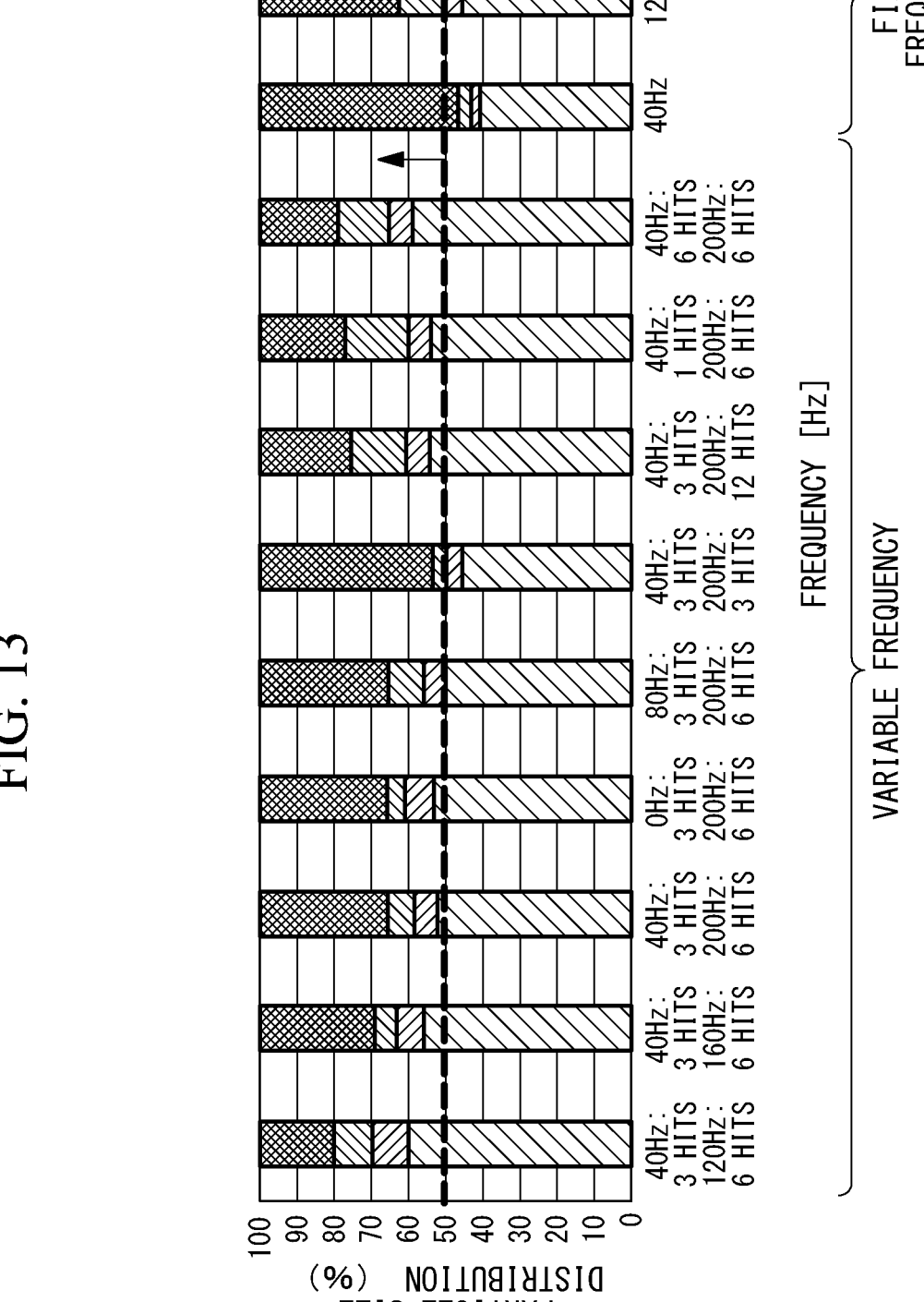
FIG. 13 illustrates an example of a particle-size distribution in a case where the frequency is variable and a case where the frequency is fixed.

FIG. 13 illustrates a comparison between a dusting effect in a case where the frequency is variable and a dusting effect in a case where the frequency is fixed. In FIG. 13, a black dashed line drawn at a position where the particle-size distribution is 50(%) is based on 120 Hz, which is a fixed frequency and is where the dusting efficiency is at a maximum. It is clear from FIG. 13 that the dusting effect is higher when the frequency is variable than any of the fixed frequency values.

For example, with regard to a fixed frequency of 40 Hz and a fixed frequency of 200 Hz, the pulling effect and the stirring effect on the stone S are not reflected on the dusting efficiency by using each of these fixed frequencies alone. However, by using a combination of 40 Hz and 200 Hz, the two effects are reflected on the improvement of the dusting efficiency. By increasing the pulse number of one of the frequencies, the property thereof becomes closer to the fixed frequency. Thus, it is preferable that the pulse number N be set between 1 and 100.

FIG. 13 corresponds to a test performed by using a device having a fiber end which is fixed to face vertically downward at an uppermost position of ten accumulated 2-mm-square stones with a 5:1 ratio of plaster and water in a state where the ten stones are immersed in pure water contained within a 10-mm-diameter tube. In detail, the uppermost position is a height position located 4 mm from the bottom of the tube. The laser used is a thulium fiber laser (TLR-50/500-QCW AC, IPG Photonics). As the laser conditions, the pulse energy is 0.2 J, the peak power is 500 W, the pulse width is 0.4 ms, the pulses are rectangular, and the total energy is 2.4 kJ.

Figure 14:
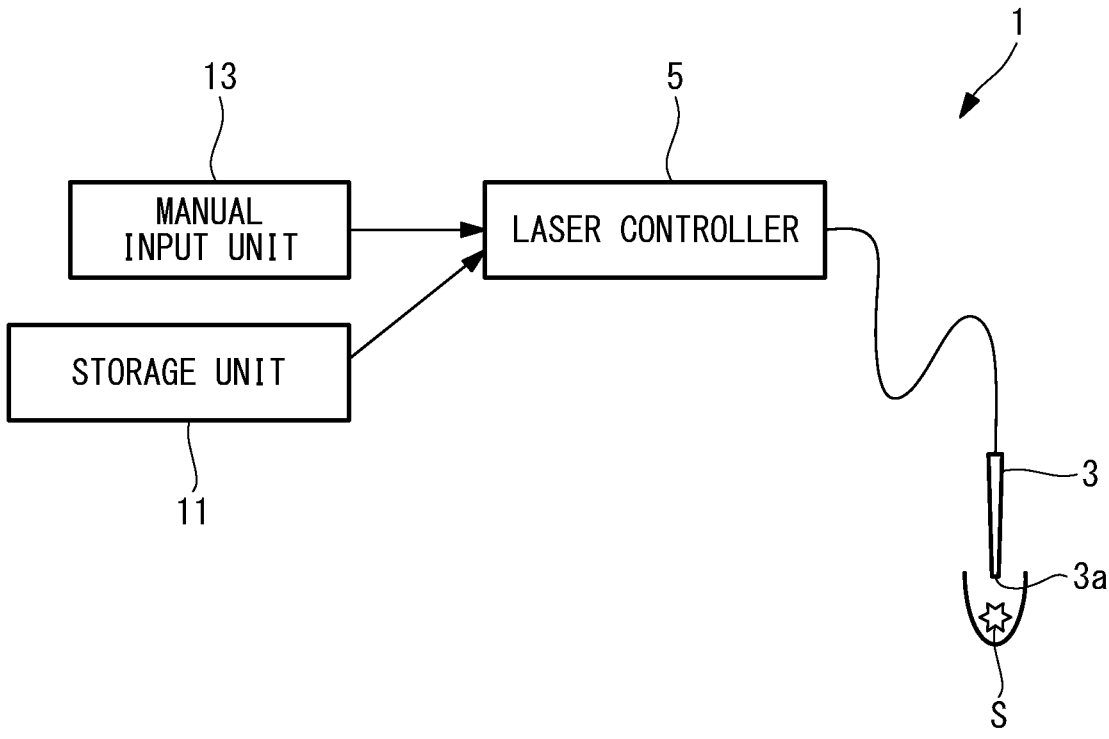
FIG. 14 schematically illustrates the configuration of a laser light irradiation system according to a modification of the embodiment of the present invention.

In this embodiment, the control condition set by the determination unit 9 is employed for controlling the frequency of the laser light. Alternatively, for example, as shown in FIG. 14, the laser light irradiation system 1 need not be equipped with the sensor 7 and the determination unit 9, and a control condition input by the user via the manual input unit 13 may be employed, or a control condition stored in the storage unit 11 may be employed. In these cases, step S3 and step S4 may be executed based on each control condition. If a control condition stored in the storage unit 11 is to be employed, the first frequency and the second frequency can be set more quickly and more easily.

Furthermore, in this embodiment, the second laser light is radiated after the first laser light is radiated. Alternatively, the first laser light, that is, the laser light of the first pulse train, may be emitted after the second laser light, that is, the laser light of the second pulse train, is emitted. Specifically, the laser controller 5 may cause the second laser light to be emitted at least before or after the emission timing of the first laser light.

Furthermore, in this embodiment, the switching between the first laser light and the second laser light is repeatedly performed. If the stone S is to be dusted into a desired size, the switching between the first laser light and the second laser light may be performed only once.

Furthermore, in this embodiment, the frequency of the laser light is switched between the first frequency and the second frequency. Alternatively, the laser controller 5 may perform the switching among three or more frequencies in addition to the first frequency and the second frequency.

Figure 15:
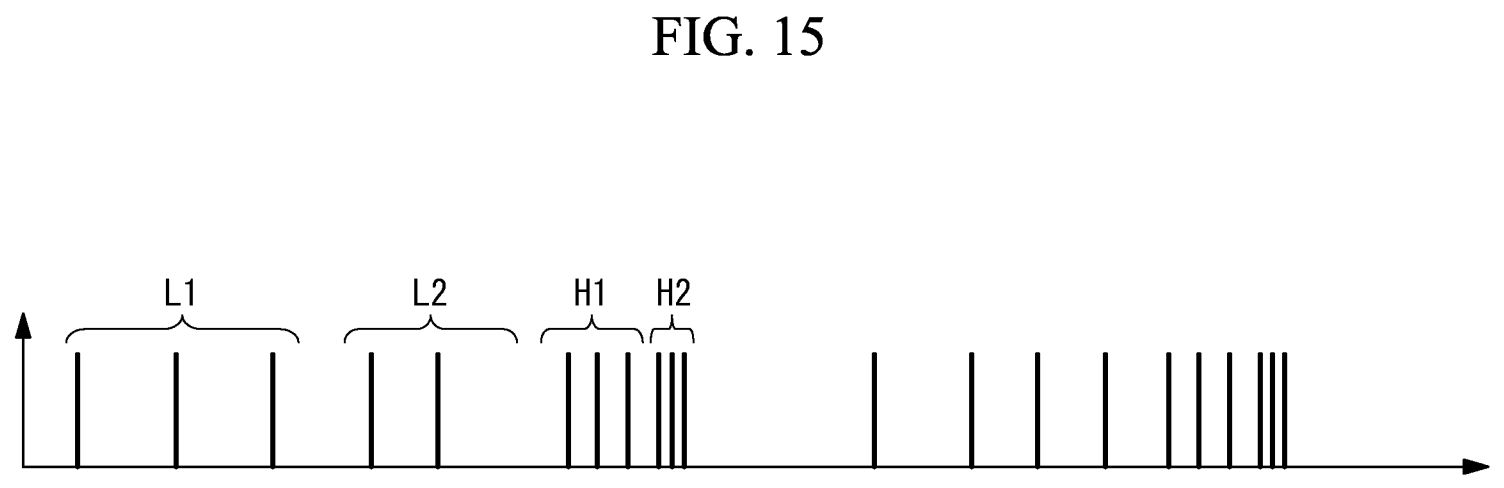

Furthermore, in this embodiment, the first laser light is emitted for the fixed time period and the second laser light is subsequently emitted for the remaining fixed time period during a specific cycle. However, the embodiment is not limited to this. For example, as shown in FIG. 15, the first frequency may be realized by two low frequencies (L1 and L2) having different interval lengths from each other. Likewise, the second frequency may be realized by two high frequencies (H1 and H2) having different interval lengths from each other.

Figure 16:
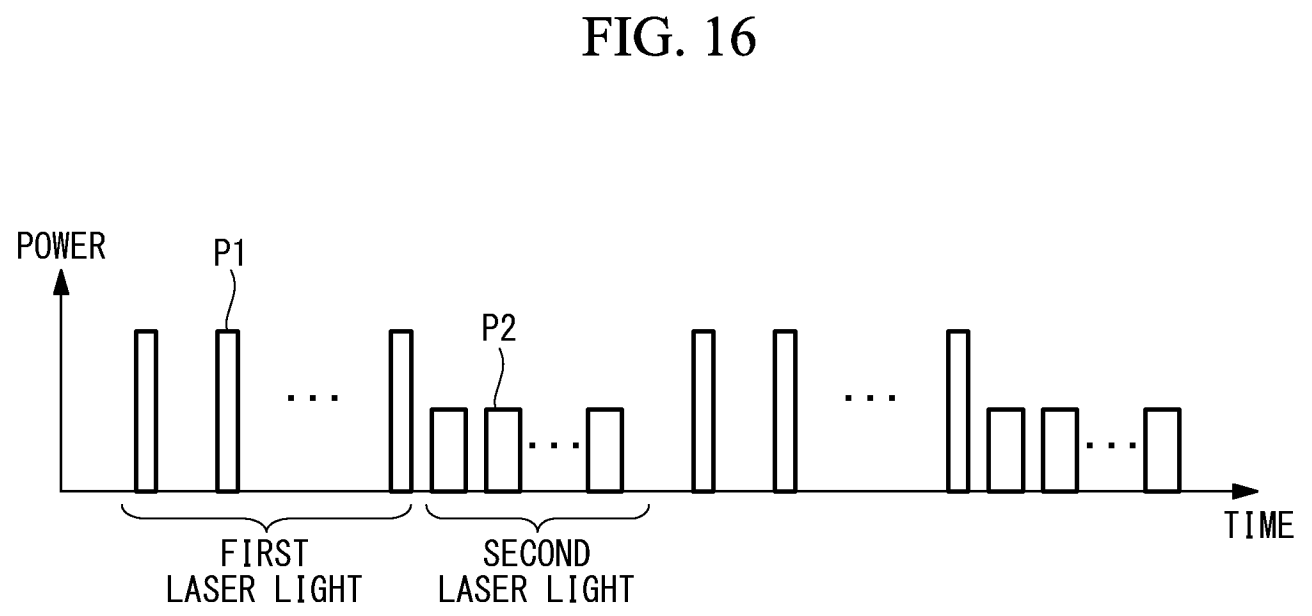

Furthermore, in this embodiment, the laser light is emitted in a state where laser conditions other than the frequency, such as the peak power and the pulse width, are fixed. However, the embodiment is not limited to this. For example, as shown in FIG. 16, at least one of the peak power of a pulse P1 and a pulse P2, the pulse width, and the frequency may be varied, so long as the laser conditions do not impair the pulling effect on the stone S by the first laser light and the stirring effect by the second laser light with the average power ranging between 10 W and 30 W. Moreover, the stirring effect may be adjusted in accordance with the flow rate of a perfusate, such as water or a physiological saline solution.

When the peak power increases, the bubble generated from the fiber emission end 3a becomes larger. Furthermore, an increase in the pulse width leads to an increase in the number of bubbles repeatedly generated and disappear with a single pulse. Since such phenomena affect the pulling effect and the stirring effect on the stone S, a process for optimizing the laser conditions is executed in the determination unit 9 so as to vary not only the frequency but also the peak power, the pulse width, or the amount of perfusion. If the type of stone S is different, the hardness and the density of the stone S are also different due to a different composition thereof, so that the manner in which the stone S is dusted also changes. Therefore, the detection of the type of stone S is useful for optimizing the frequency, the peak power, and the pulse width.

In this embodiment, the determination unit 9 may determine whether or not the stone S has been dusted to a size smaller than a predetermined threshold value based on information related to the state of the stone S. Then, if it is determined that the stone S has not been dusted to the size smaller than the predetermined threshold value, steps S2 to S4 may be repeated. Furthermore, if it is determined that the stone S has been dusted to the size smaller than the predetermined threshold value, the determination unit 9 may command the laser controller 5 to end the laser irradiation.

Although this embodiment relates a stone in the urinary tract as an example, the pulse train effect is not limited to a urinary-tract stone treatment and can be similarly achieved with respect to a stone in a bile duct. Furthermore, this embodiment is not limited to a stone in the urinary tract, and may be applicable to a treatment on any living tissue in water, an aqueous solution, an organic solution, or the air.

Although the embodiment of the present invention has been described above in detail with reference to the drawings, specific configurations are not limited to the embodiment, and design modifications are included so long as they do not depart from the scope of the invention. For example, the present invention is not limited to the embodiment and modifications described above, and may be applied to an embodiment obtained by appropriately combining the above embodiment and modifications; the invention is not particularly limited.

REFERENCE SIGNS LIST 1 laser light irradiation system
3 laser fiber
3a fiber emission end
5 laser controller (controller)
7 sensor
11 storage unit
B bubble
S stone

The invention claimed is:
1. A laser light irradiation system comprising:
a laser fiber that delivers laser lights from a light source; and
a sensor configured to output information comprising a detection of a state of a stone in a body and a state of a closed space to be irradiated with the laser lights, a processor configured to:

control the light source to emit a series of first laser lights having a first frequency;

control the light source to emit a series of second laser lights having a second frequency, different from the first frequency, before or after an emission timing of the first laser light; and switch between the first laser lights and the second laser lights based on the information output by the sensor, wherein:

the first laser lights are configured to, one of, generate a water flow that pulls the stone toward the laser fiber or generate a water flow that stirs the stone; and the second laser lights are configured to perform the alternate one of, generate a water flow that pulls the stone toward the laser fiber or generate a water flow that stirs the stone.

2. The laser light irradiation system according to claim 1, wherein the processor is configured to switch the first frequency to a frequency lower than the second frequency.

3. The laser light irradiation system according to claim 1, wherein a frequency of the first laser lights are a frequency at which next first laser lights are emitted in a state where the stone pulled toward the laser fiber in accordance with irradiation of previous first laser lights are disposed in an irradiation range of the first laser lights.

4. The laser light irradiation system according to claim 1, wherein average power of the first laser lights light and the second laser lights are between 10 W and 30 W.

5. The laser light irradiation system according to claim 1, wherein the first frequency or second frequency is lower than or equal to 120 Hz.

6. The laser light irradiation system according to claim 1, wherein the state of the stone includes at least one of a size, number, type, and shape thereof.

7. The laser light irradiation system according to claim 1, wherein the state of the space includes at least one of a size, shape, and gravitational direction of the space.

8. The laser light irradiation system according to claim 1, wherein the sensor is a camera configured to acquire an image of the stone.

9. The laser light irradiation system according to claim 1, wherein the processor is configured to repeat emission of the first laser lights and the second laser lights are based on the information which is related to a size of the stone and which is output by the sensor.

10. The laser light irradiation system according to claim 1, further comprising:

a storage unit configured to store a plurality of control conditions for controlling the frequency of the laser lights, wherein the processor is configured to control the frequency of the laser lights based on the control conditions stored in the storage unit.

11. The laser light irradiation system according to claim 1, wherein the first laser lights includes a first pulse train and the second laser lights includes a second pulse train which is different from the first pulse train.

12. A laser light irradiation method for irradiating a stone in a body with laser lights to cause the stone to be dust, the laser light irradiation method comprising:

receiving information comprising a detection of a state of the stone and a state of a closed space to be irradiated with first laser lights and second laser lights;

controlling the first laser lights having a first frequency configured to generate a water flow that pulls the stone toward a fiber emission end from which the laser lights are emitted in a series;

controlling the second laser lights having a second frequency configured to generate a water flow that stirs the stone at least before or after an emission timing of the first laser lights in a series; and switching between controlling the first laser lights and the second laser lights based on the received information.

13. The laser light irradiation method according to claim 12, wherein the frequency of the first laser lights are lower than the frequency of the second laser lights.

14. The laser light irradiation method according to claim 12, wherein the frequency of the first laser lights are a frequency at which next first laser lights are emitted in a state where the stone pulled toward the fiber emission end in accordance with irradiation of previous first laser lights are disposed in an irradiation range of the first laser lights.

15. The laser light irradiation method according to claim 12, wherein average power of the first laser lights and the second laser lights are between 10 W and 30 W.

16. The laser light irradiation method according to claim 12, wherein the first frequency is lower than or equal to 120 Hz.

17. A method for causing a stone in a body to be dust, the method comprising:

receiving information comprising a detection of a state of the stone and a state of a closed space to be irradiated with first laser lights or second laser lights, positioning a laser fiber to be directed to the stone, the laser fiber being configured to emit a series of the first laser lights;

keeping the laser fiber at a position while an operation is being performed, the operation making the first laser lights emit from the laser fiber configured to generate a water flow that pulls the stone toward the laser fiber; and switching, based on the received information, to emit a series of the second laser lights configured to generate a water flow for stirring the stone before or after an emission timing of pulling the stone toward the laser fiber.

18. The method according to claim 17, further comprising:

switching the emission of the second laser lights to emission of the first laser lights when the stone moves into a range by the emission of the second laser lights, the range being one where a suction effect is generated by the first laser lights.

19. The method according to claim 17, wherein the switching of the emission of the first laser lights and the emission of the second laser lights are repeated until a size of the stone becomes smaller than a predetermined size.

* * * * *